United States Patent [19]

Shepherd

[11] 4,309,553

[45] Jan. 5, 1982

[54] ALDEHYDES AND KETONES CONTAINING A 4-(MONOALKYLAMINO)-BENZOYL SUBSTITUENT

[75] Inventor: Robert G. Shepherd, South Nyack, N.Y.

[73] Assignee: American Cyanamid Company, Stamford, Conn.

[21] Appl. No.: 156,144

[22] Filed: Jun. 3, 1980

Related U.S. Application Data

[62] Division of Ser. No. 836,947, Sep. 27, 1977, Pat. No. 4,273,785.

[51] Int. Cl.$^3$ .................. C07D 317/28; C07D 319/06; C07D 327/04; C07D 329/08
[52] U.S. Cl. .................................... 549/22; 260/340.7; 260/340.9 R; 549/14; 549/30; 549/35; 549/39
[58] Field of Search ..................... 260/340.7, 340.9 R; 549/14, 22, 30, 35, 39

[56] References Cited

U.S. PATENT DOCUMENTS

| 2,690,988 | 10/1954 | Jones et al. | 549/35 |
| 4,042,601 | 8/1977 | Wilson et al. | 549/30 |
| 4,111,960 | 9/1978 | Sam | 260/340.9 R |

Primary Examiner—Richard Raymond
Attorney, Agent, or Firm—Jack W. Richards

[57] ABSTRACT

This disclosure describes novel aldehydes and ketones containing a 4-(monoalkylamino)phenyl moiety, derivatives and salts thereof, useful as hypolipidemic and antiatherosclerotic agents.

8 Claims, No Drawings

ALDEHYDES AND KETONES CONTAINING A 4-(MONOALKYLAMINO)-BENZOYL SUBSTITUENT

This is a division of application Ser. No. 836,947, filed Sept. 27, 1977, now U.S. Pat. No. 4,273,785.

BRIEF SUMMARY OF THE INVENTION

This invention relates to new organic compounds and, more particularly, is concerned with aldehydes and ketones containing a monoalkylaminobenzoyl moiety, derivatives and salts thereof, which may be represented by the following structural formula:

$$R_1-N(R_2)-C_6H_4-Z-R_3$$

wherein $R_1$ is a straight chain or branched alkyl group of the formula $C_nH_{2n+1}$ wherein n is an integer from 8 to 19, inclusive;

$R_2$ is hydrogen or a group convertible in vivo thereinto such as methyl, ethyl, carboxymethyl, lower alkanoyl ($C_1$-$C_6$), succinyl, 1-(sodium sulfo)lower alkyl, 1-(sodium sulfo)polyhydroxyalkyl or 1,3-bis-(sodium sulfo)aralkyl;

$R_3$ is selected from the group consisting of hydrogen, alkyl having up to 6 carbon atoms with the proviso that when Z is carbonyl then $R_3$ may not be methyl, diazomethyl, oxymethyl, lower alkanoyloxymethyl, phenyl, substituted phenyl, phenyl lower alkyl and substituted phenyl lower alkyl;

and Z is a divalent radical selected from the group consisting of those of the formula:

$$\begin{array}{c}\text{C=O,} \quad \text{C(OH)(SO}_3\text{Na)}, \\ \text{C(SR}_4\text{)}_2, \quad \text{C(SCH}_2\text{C}_6\text{H}_5\text{)}_2, \quad \text{C(SCH}_2\text{COOR}_4\text{)}_2, \\ \text{C(O-CHR}_5\text{-O-CH}_2\text{)}, \quad \text{C(NH-CHR}_5\text{-S-CH}_2\text{)}, \quad \text{C(O-CHR}_5\text{-S-CH}_2\text{)}, \\ \text{C(OCH}_2\text{COOR}_4\text{)}_2, \quad \text{C(O-CH}_2\text{-CH}_2\text{-O-CH}_2\text{)}, \\ \text{C(S-CH}_2\text{-CH}_2\text{-S-CH}_2\text{)}, \quad \text{C(NH-CHR}_5\text{-O-CH}_2\text{)}, \\ \text{C(S-CHR}_5\text{-S-CH}_2\text{)}, \quad \text{C=N-O-R}_4, \quad \text{C=N-NR}_4\text{R}_4, \\ \text{C=N-NH-CONH}_2, \quad \text{C=N-CH}_2\text{COOR}_4,\end{array}$$

-continued $$\text{C=N-NH-CH}_2\text{COOR}_4 \text{ and } \text{C=N-C}_6\text{H}_4\text{-COOH}$$

wherein $R_4$ is hydrogen or alkyl having up to 4 carbon atoms and $R_5$ is hydrogen, carboxy, carboxymethyl, hydroxymethyl or alkyl having up to 3 carbon atoms.

A preferred embodiment of this invention consists of those compounds in which n is an integer from 14 to 19, inclusive, either in the free or derivatized state, namely compounds of the formula:

$$CH_3(CH_2)_{13-18}-NH-C_6H_4-C(=O)-R_3$$

wherein $R_3$ is as previously defined.

A more preferred embodiment of this invention consists of those compounds in which n is the integer 16, either in the free or derivatized state, namely compounds of the formula:

$$CH_3(CH_2)_{15}-NH-C_6H_4-C(=O)-R_3$$

wherein $R_3$ is as previously defined.

The straight chain alkyl groups for the substituent $R_1$ may be, for example, octyl, nonyl, decyl, undecyl, dodecyl, tridecyl, tetradecyl, pentadecyl, hexadecyl, heptadecyl, octadecyl and nonadecyl. Suitable branched alkyl groups for the substituent $R_1$ may be, for example, 1-methylpentadecyl, 1-ethyltetradecyl, 1-heptylnonyl, 2-ethyldodecyl, 1,4-diethyloctyl, 11-methyldodecyl, 5,5-dimethylhexyl, 4,8,12-trimethyltridecyl, 2,4,5,8-tetramethylnonyl, 1,4-dimethyl-1-ethylhexyl, 13,13-dimethyltetradecyl, 15,15-dimethylhexadecyl, and the like. Suitable lower alkyl and lower alkoxy groups contemplated by this invention are those having up to 6 carbon atoms, as for example, methyl, ethyl, isopropyl, propyl, tert-amyl, tert-butyl, methoxy, ethoxy, isobutoxy, n-amyloxy, and the like. Suitable phenyl and substituted phenyl groups include, for example, phenyl, 4-lower alkoxyphenyl, 4-hydroxyphenyl, 3-carbethoxyphenyl, 4-carboxyphenyl, 4-benzyloxyphenyl, 4-lower alkylphenyl, 2,4-di(lower alkyl)phenyl, etc. Suitable phenyl, 2,4-di(lower alkyl) phenyl, etc. Suitable phenyl lower alkyl and substituted phenyl lower alkyl groups include, for example, benzyl, α-phenylethyl, β-phenylethyl, and substituted benzyl such as 4-lower alkoxybenzyl, 2,4-dilower alkoxybenzyl, 4-carboxybenzyl, 4-lower alkylbenzyl, 2,4-di(lower alkyl)benzyl, etc.

The invention also pertains to novel compositions of matter useful as antiatherosclerotic agents and to methods of meliorating atherosclerosis by counteracting hyperlipemia and arterial plaque formation in mammals therewith; the active ingredients of said compositions of matter being the novel aldehydes and ketones of the present invention in the free form or in the derivatized form or in the form of a pharmaceutically acceptable salt with an organic or inorganic acid or base. The invention also contemplates a method for lowering serum lipids and for meliorating atherosclerosis in mammals by the administration of said aldehydes and ketones.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in their initiation and development and also, more importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson & Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the part, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [(Levy & Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

U.S. Pat. No. 3,868,416 discloses and claims certain 4-(monoalkylamino)benzoic acids and esters, pharmaceutically acceptable salts, pharmaceutical compositions thereof and a method of lowering serum lipid levels in mammals therewith. No prior art is known which discloses aldehydes and ketones containing a monoalkylaminobenzoyl moiety, derivatives and salts thereof of this invention and no hypolipidemic activity has been reported in the literature for these compounds and they are different in structure from other hypolipidemic agents. The compounds of this invention lower serum-lipid concentrations and also minimize atheroma formation in the aorta. These 4-(monoalkylamino)phenyl aldehydes and ketones provide the oral administration required of hypolipidemic agents, which patients usually take for many years. The novel compounds of this invention are absorbed from the gastrointestinal tract and do not cause gastrointestinal irritation. The anti-atherogenic activity of alkylaminobenzoic acids has been announced; Abstract No. 27, American Oil Chemists Society, 67th Meeting, New Orleans, Apr. 21–24, 1976; Federation Proceedings 36, Abstract No. 4706 (1977).

We have now found that members of this class of compounds can safely and effectively lower both serum sterols and triglycerides in warm-blooded animals. Such action on serum lipid components are considered to be very useful in the tratment of atherosclerosis, especially in contrast to available drugs whose action is much more limited. For some time it has been considered desirable to lower serum lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm blooded mammals for the treatment of hyperlipidemic and atherosclerotic states found in patients with or prone to heart attacks, to peripheral or cerebral vascular disease, and to stroke.

The 4-(monoalkylamino)phenyl aldehydes and ketones of the present invention are, in general, white crystalline solids having characteristic melting points and spectral characteristics. They are soluble in organic solvents such as lower alkanols, chloroform, benzene, diemethylformamide, and the like, but are generally insoluble in water.

The novel compounds of the present invention form non-toxic acid-addition salts with a variety of pharmacologically acceptable inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, and the like. For purposes of this invention the free bases are equivalent to their non-toxic acid-addition salts. The acid-addition salts of the organic bases of the present invention are, in general, crystalline solids. The carboxyl-containing compounds from pharmaceutically acceptable cationic salts with bases such as the alkali metal hydroxides, the alkaline earth metal hydroxides, and the like.

The free aldehydes of this invention may be prepared by di-isobutylaluminum hydride treatment with stirring of the corresponding benzonitrile in an aromatic solvent such as toluene at 10°–50° C. over a period extending from ½ hour to 5 hours. After destruction of the excess hydride, the product is isolated directly or indirectly by extraction. The product is purified by recrystallization from organic solvents such as the hexanes, cyclohexane and the like. The aldehydes may also be prepared by catalytic hydrogenation of metal hydride reduction of a suitably protected acid chloride such as N-carbobenzyloxy-4-(hexadecylamino)benzoyl chloride or of an amide such as 4-(hexadecylamino)benzoyl dimethylamide. The acid chlorides such as the above may also be used to form the aldehydes by reacting them with potassium cyanide and quinoline or, alternatively, with toluenesulfonyl hydrazide followed by alkali and heat. The aldehydes are also made by reaction of a suitably N-protected N-alkylaniline with dimethylformamide and phosphorus oxychloride, thereby introducing the aldehyde group onto the ring.

The aldehydes of this invention are also prepared by alkylation of suitable cyclic or acyclic acetals such as 4-aminobenzaldehyde ethyleneacetal with alkyl halides or mesylates. The free aldehyde is then formed by hydrolysis of the acetal. The compounds of this invention are also synthesized by reductive alkylation of aldehydes, ketones or their acetals with suitable carbonylalkanes and catalytic or chemical reduction and by diborane reduction of their N-alkanoyl derivatives. These reductive procedures can also employ compounds containing groups serving as precursors of the amino group such as nitro groups and the like.

The free ketones of this invention may generally be prepared by reacting p-aminoacetophenone and the like with a bromoalkane is an organic solvent such as hexamethylphosphoramide with an acid acceptor such as potassium carbonate for 8 to 24 hours at 75°–125° C. The product is isolated directly or indirectly by extraction. The product is purified by recrystallization from organic solvents such alcohols, dichloromethane and the like.

The oxyacetyl compounds of the present invention are prepared from the corresponding benzoic acid which is initially converted into its acid chloride hydrochloride with a reagent such as thionyl chloride, at 0°–5° C. Treatment of these acid chlorides with diazomethane at 0° C. generates the diazoketones. Reaction of the latter with mineral acids in solvents such as tetrahydrofuran provides the free oxyacetyl compounds which may be isolated by extraction and chromatography. Reaction of the diazoketones with aliphatic acids such as acetic acid and pivalates give the corresponding alkanoyl esters which may be isolated by extraction and chromatography.

The 4-monoalkylamino-oxyacetophenones N,O-diacylates can be prepared by acylation of the free compounds with acyl halides or anhydrides such as acetyl chloride, acetic anhydride, benzoyl chloride, benzoic anhydride, succinic anhydride, etc. in the presence of a suitable base as pyridine, triethylamine and the like with or without an organic solvent.

Certain derivatives

of the aminophenyl nitrogen atom are useful for providing greater solubility, more uniform and reliable intestinal absorption, and for a certain degree of modification of the pharmacology of the compounds of the present invention. Some of these derivatives can be converted to the corresponding N—H forms by the acidity of the stomach or the alkalinity of the small intestine. Others are converted by metabolic processes. The methyl and carboxymethyl derivatives and the like are prepared by the alkylation, reductive alkylation and acylamino reduction methods above. Derivatives such as the acetyl and succinyl compounds may be prepared using acetyl chloride, acetic anhydride, succinic anhydride, etc. in the presence of pyridine, triethylamine or the like at temperatures moderate enough to avoid acylation of the amide moiety. The 1-(sodium sulfo)alkyl derivatives are obtained by reaction of the 4-(monoalkylamino)-phenyl derivatives, or suitable intermediates in certain cases, with sodium bisulfite and an aliphatic aldehyde, a polyhydroxyaldehyde such as glyceraldehyde or glucose, or cinnamaldehyde in a mixed organic-aqueous medium. In the case of cinnamaldehyde, the di-sulfonate salts result from addition of the bisulfite to the carbon-nitrogen double bond of the anil intermediate as well as to the carbon-carbon of cinnamaldehyde itself.

The novel compounds of the present invention are not only hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 grams to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the compound may be administered conveniently by the oral route. It is not known how these novel compounds operate in the blood serum and no theory of why these compounds so operate is advanced. It is not intended that the present invention should be limited to any particular mechanism of action of lowering serum lipids or of meliorating atherosclerosis, or be limited to compounds acting by only one mechanism.

The compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixers, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1 p-Hexadecylaminobenzaldehyde p-Aminobenzonitrile (11.8 g., 0.1 mole) and 1-bromohexadecane (15.25 g., 0.05 mole) are dissolved in hexamethylphosphoramide (200 ml.) and heated under nitrogen in an oil bath maintained at 120° C. for 22 hours. The reaction mixture is cooled to room temperature and water (50 ml.) is added gradually. The mixture is then chilled in an ice-bath. The precipitate separated is filtered, washed thoroughly with water, and dried. It is then washed repeatedly with hexane and dried. The 14.2 g. of pale brownish yellow granular solid is obtained as a homogeneous product. Recrystallization from ether-hexane affords p-hexadecylaminobenzonitrile as a pale yellow prisms, m.p. 63°–64° C.

Di-isobutylaluminum hydride (54-ml., 25% solution in toluene) is added with stirring to a solution of p-hexadecylaminobenzonitrile (11.4 g.) under a nitrogen atmosphere. The temperature rises to 40° C. during the addition which takes 30 minutes and the reaction is then stirred for 1 hour. A solution of methanol in toluene (50 ml., 1:1) is added over 30 minutes and the mixture is poured into vigorously stirred ice-cold aqueous sulfuric acid (500 ml., 5%). After 10 minutes diatomaceous earth (30 g.) is added, the mixture filtered and the organic layer separated. The aqueous solution is extracted twice with toluene (100 ml.) and the combined organic layers are washed with aqueous sodium bicarbonate, dried over magnesium sulfate, decolorized with charcoal, filtered and evaporated in vacuo to give a light yellow crystalline solid. The crude product is dissolved in dichloromethane and filtered through hydrated magnesium silicate (80 g.) to give a white crystalline material on removal of the solvent. The product is recrystallized from dichloromethane/hexanes giving colorless fine needles (6.0 g.), m.p. 84°–85° C.

EXAMPLE 2 p-Octylaminobenzaldehyde

Following the procedure of Example 1 employing 1-bromooctane provides p-octylaminobenzonitrile which in turn provides the product of the Example.

EXAMPLE 3 p-Tetradecylaminobenzaldehyde

Following the procedure of Example 1 employing 1-bromotetradecane provides p-tetradecylaminobenzonitrile which in turn provides the product of the Example.

EXAMPLE 4

1-Bromo-15-methyl hexadecane

A solution of 3-methylbutylmagnesium bromide is prepared by treating 15.1 g. (0.1 mole) of 3-methylbutylbromide with 2.7 g. (1.1 equivalents) of magnesium turnings in 50 ml. of dry tetrahydrofuran. The resulting Grignard reagent is added dropwise to a solution of 36.1 g. (1.1 equivalents) of 1,12-dibromododecane and 0.2 g. (1 millimole) of lithium copper chloride in 75 ml. of dry tetrahydrofuran. The solution is stirred for 1 hour, evaporated, and fractionally distilled in vacuo to yield the product of the Example as a colorless liquid.

By a procedure analogous to that described above, 3-methylbutyl magnesium bromide in tetrahydrofuran is reacted with 34.5 g. (0.11 moles) of 1,11-dibromoundecane and 0.2 g. of lithium copper chloride in 75 ml. of tetrahydrofuran. After 1 hour stirring at −10° C., the solution is evaporated, and the resultant oil is distilled in vacuo to yield the colorless 1-bromo-14-methylpentadecane.

EXAMPLE 5 p-(14-Methylpentadecyl)aminobenzaldehyde

Following the procedure of Example 1 employing 1-bromo-14-methylpentadecane provides p-(14-methylpentadecylamino)benzonitrile which in turn provides the product of the Example.

EXAMPLE 6 p-(15-Methylhexadecylamino)benzaldehyde

Following the procedure of Example 1 employing 1-bromo-15-methylhexadecane provides p-(15-methylhexadecylamino)benzonitrile which in turn provides the product of the Example.

EXAMPLE 7 p-(1-Methylundecylamino)benzaldehyde

Following the procedure of Example 1 employing 2-bromododecane provides the benzonitrile which in turn provides the product of the Example.

EXAMPLE 8 p-Heptadecylaminobenzaldehyde

Following the procedure of Example 1 employing 1-bromoheptadecane provides p-heptadecylaminobenzonitrile which in turn provides the product of the Example.

EXAMPLE 9 p-Nonadecylaminobenzaldehyde

Following the procedure of Example 1 employing 1-bromononadecane provides p-nonadecylaminobenzonitrile which in turn provides the product of the Example.

EXAMPLE 10 p-Hexadecylaminobenzaldehyde Hydrochloride

Hydrogen chloride is bubbled with stirring into a solution of p-hexadecylaminobenzaldehyde (1 g.) in anhydrous diethyl ether (50 ml.). Immediately a white precipitate forms, and after 3 minutes the mixture is filtered and washed several times with anhydrous diethyl ether to provide the product of the Example.

EXAMPLE 11 p-Hexadecylaminoacetophenone p-Aminoacetophenone (87.6 g.) is heated with 1-bromohexadecane (198 g.) in dry hexamethyl phosphoramide (300 ml.) containing anhydrous potassium carbonate (90 g.) for 16 hours at 100° C. The solution is cooled to room temperature, filtered to remove solids, and the filtrate is diluted with cold water (20 ml.). The amber solid so obtained is collected and washed with water. Recrystallization from ethanol followed by dichloromethane provides the product of the Example.

EXAMPLE 12 p-Octylaminocetophenone

Following the procedure of Example 11 employing 1-bromooctane provides the product of the Example.

EXAMPLE 13 p-Tetradecylaminoacetophenone

Following the procedure of Example 11 employing 1-bromotetradecane provides the product of the Example.

EXAMPLE 14 p-Pentadecylaminoacetophenone

Following the procedure of Example 11 employing 1-bromopentadecane provides the product of the Example.

EXAMPLE 15 p-Octadecylaminoacetophenone

Following the procedure of Example 11 employing 1-bromooctadecane provides the product of the Example.

EXAMPLE 16 p-Hexadecylamino-2-oxyacetophenone

A. To 90 ml. of thionyl chloride cooled to 0° C. was added portionwise 21.7 g. (0.060 mole) of p-hexadecylaminobenzoic acid. To the viscous mass was added 100 ml. of toluene. After stirring overnight (16.5 hours) the solvent was removed in vacuo. Toluene (50 ml.) was added and the solvent was removed in vacuo. This provides p-hexadecylaminobenzoyl chloride hydrochloride as an amber oil.

To an ether solution of four equivalents of diazomethane is added dropwise at 0° C. with stirring a solution of one equivalent of p-hexadecylaminobenzoyl chloride hydrochloride in dimethoxyethane and/or tetrahydrofuran.

The reaction mixture is stirred for 1 hour, when the solvent and excess diazomethane are removed in a stream of nitrogen. The resulting diazoketone is refluxed in a mixture of tetrahydrofuran and dilute sulfuric acid for 10 hours. The mixture is poured into brine and extracted with tetrahydrofuran. The organic layer is dried over magnesium sulfate, and evaporated in vacuo. The residue is purified by column chromatography on silica gel to provide the product of the Example.

B. Two grams of p-hexadecylamino-2-oxyacetophenone O-acetate in 150 cc. of methanol is treated with a solution of 2 g. of potassium bicarbonate in 40 cc. of water, and the mixture is refluxed for 1 hour. The reaction mixture is then concentrated in vacuo. The solid is collected and washed copiously with water to provide the product of the Example.

EXAMPLE 17

4'-Glycolyl-N-hexadecylacetanilide Acetate (p-Hexadecylamino-2-oxyacetophenone N,O-diacetate)

A. p-Hexadecylamino-2-oxyacetophenone (0.3 g.) in pyridine (2 ml.) is treated with acetic anhydride (1 ml.), and the mixture is allowed to stand at room temperature for 3 hours. It is then poured into cold-water, and the product of the Example is collected by filtration.

B. p-Hexadecylamino-2-oxyacetophenone O-acetate (0.3 g.) in pyridine (2 ml.) is treated with acetic anhydride (1 ml.), and the mixture is allowed to stand at room temperature for 3 hours. It is then poured into cold-water, and the product of the Example is collected by filtration.

EXAMPLE 18 p-Hexadecylamino-2-oxyacetophenone O-Acetate

The diazoketone prepared according to Example 16 is added to boiling glacial acetic acid (purified by treatment with potassium permanganate). An immediate evolution of nitrogen results. After refluxing for 5 minutes the acetic acid is evaporated under reduced pressure, and the residue is purified by column chromatography on silica gel to provide the product of the Example.

EXAMPLE 19 p-Hexadecylamino-2-oxyacetophenone O-Propionate

Following the procedure of Example 16 the diazoketone is added to a refluxing solution of propionic acid in dimethoxyethane (b.p. 64° C.). An immediate evolution of nitrogen results, and the mixture is refluxed for about 10 minutes. It is then evaporated under reduced pressure, and the residue is purified by column chromatography on silica gel to provide the product of the Example.

EXAMPLE 20 p-Hexadecylamino-2-oxyacetophenone O-Pivalate

Following the procedure of Example 16 the diazoketone is added to a refluxing solution of pivalic acid in dimethoxyethane (b.p. 64° C.). An immediate evolution of nitrogen results, and the mixture is refluxed for about 10 minutes. It is then evaporated under reduced pressure, and the residue is purified by column chromotography on silica gel to provide the product of the Example.

EXAMPLE 21 p-Hexadecylamino-2-oxyacetophenone O-Acetate Hydrochloride

Hydrogen chloride is bubbled with stirring into a solution of p-hexadecylamino-2-oxyacetophenone O-acetate (1 g.) in anhydrous diethyl ether (50 ml.). Immediately a white precipitate forms, and after 3 minutes the mixture is filtered and washed several times with anhydrous diethylether to provide the product of the Example as a white solid.

EXAMPLE 22 p-Octadecylamino-2-oxyactophenone

Following the procedure of Example 16 employing p-octylaminobenzoic acid, the product of the Example is formed.

EXAMPLE 23 p-Undecylamino-2-oxyacetophenone

Following the procedure of Example 18 employing p-undecylaminobenzoic acid provides p-undecylamino-2-oxyacetophenone O-acetate.

Saponification with potassium bicarbonate is methanol according to the procedure of Example 16 B generates the product of the Example.

EXAMPLE 24 p-Tridecylamino-2-oxyacetophenone

Following the procedure of Example 18 employing p-tridecylaminobenzoic acid provides p-tridecylamino-2-oxyacetophenone O-acetate.

Saponification with potassium bicarbonate in methanol according to the procedure of Example 16 B generates the product of the Example.

EXAMPLE 25 p-Dodecylamino-2-oxyacetophenone

Following the procedure of Example 18 employment p-dodecylaminobenzoic acid provide p-dodecylamino-2-oxyacetophenone O-acetate.

Saponification with potassium bicarbonate in methanol according to the procedure of Example 16 B generates the product of the Example.

EXAMPLE 26 p-Tetradecylamino-2-oxyacetophenone

Following the procedure of Example 18 employing p-tetradecylaminobenzoic acid provides p-tetradecylamino-2-oxyacetophenone O-acetate.

Saponification with potassium bicarbonate in methanol according to the procedure of Example 16 B generates the product of the Example.

EXAMPLE 27 p-Pentadecylamino-2-oxyacetaphenone

Following the procedure of Example 18 employing p-pentadecylamino-2-oxyacetophenone O-acetate.

Saponification with potassium bicarbonate in methanol according to the procedure of Example 16 B generates the product of the Example.

EXAMPLE 28 p-14-Methylpentadecyl)amino-2-oxyacetophenone

Following the procedure of Example 18 employing p-(14-methylpentadecyl)aminobenzoic acid provides p-(14-methylpentadecyl)amino-2-oxyacetophenone O-acetate.

Saponification with potassium bicarbonate in methanol according to the procedure of Example 16 B generates the product of the Example.

EXAMPLE 29 p-Octadecylamino-2-oxyacetophenone

Following the procedure of Example 18 employment p-octadecylaminobenzoic acid provides p-octadecylamino-2-oxyacetophenone O-acetate.

Saponification with potassium bicarbonate in methanol according to the procedure of Example 16 B generates the product of the Example.

EXAMPLE 30 p-Nonadecylamino-2-oxyacetophenone

Following the procedure of Example 18 employing p-nonadecylaminobenzoic acid provides p-nonadecylamino-2-oxyacetophenone O-acetate.

Saponification with potassium bicarbonate in methanol according to the procedure of Example 16 B generates the product of the Example.

EXAMPLE 31 p-Hexadecylaminobenzophenone p-Aminobenzophenone (75 g.) is heated with hexadecyl bromide (200 g.) in dry hexamethylphosphoramide (300 ml.) containing anhydrous potassium carbonate (90 g.) for 16 hours at 100° C. The solution is cooled to room temperature, filtered to remove solids, and the filtrate is diluted with cold water (20 ml.). The solid so obtained is collected and washed with water. Recrystallization from ethanol followed by dichloromethane provides the product of the Example.

EXAMPLE 32 p-Undecylaminobenzophenone p-Aminobenzophenone (75 g.) is heated with undecyl bromide (200 g.) in dry hexamethyl phosphoramide (300 ml.) containing anhydrous potassium carbonate (90 g.) for 16 hours at 100° C. The solution is cooled to room temperature, filtered to remove solids, and the filtrate is diluted with cold water. The solid so obtained is collected and washed with water. Recrystallization from ethanol followed by dichloro methane provides the product of the Example.

EXAMPLE 33 p-Octadecylaminobenzophenone p-Aminobenzophenone (25 g.) is heated with octadecyl bromide (70 g.) in dry hexamethylphosphoramide (100 ml.) containing anhydrous potassium carbonate (30 g.) for 16 hours at 100° C. The solution is cooled to room temperature, filtered to remove solids, and the filtrate is diluted with cold water (10 ml.). The solid so obtained is collected and washed with water. Recrystallization from ethanol followed by dichloromethane provides the product of the Example.

EXAMPLE 34 p-Hexadecylaminobenzaldehyde Cycloethyleneketal p-Hexadecylaminobenzaldehyde (1.7 g.) is dissolved in toluene (20 ml.), and ethylene glycol (2.5 ml.) and p-toluenesulfonic acid (10 mg.) are added. The reaction is heated to reflux for 16 hours while water is removed using a Dean-Stark trap. The reaction mixture is then cooled to room temperature, diluted with toluene (70 ml.), washed once with aqueous sodium bicarbonate and then twice with water. The organic layer is then dried out magnesium sulfate, decolourized with charcoal and filtered through hydrous magnesium silicate. Removal of the solvent in vacuo gives a light yellow solid that is recrystallized from hexanes giving the product of the Example, 1.6 g., m.p. 66.5°–67.5° C.

EXAMPLE 35 p-Octylaminobenzaldehyde Cycloethylene Ketal

Following the procedure of Example 34 employing p-octylaminobenzaldehyde yields the product of the Example.

EXAMPLE 36 p-Hexadecylaminoacetophenone Cycloethylene Ketal

Following the procedure of Example 34 employing p-hexadecylaminoacetophenone gives the product of the Example.

EXAMPLE 37 p-Hexadecylamino-2-oxyacetophenone Cycloethylene Ketal

Employing the procedure of Example 34 with p-hexadecylamino-2-oxyacetophenone yielded the produce of the Example.

EXAMPLE 38 p-Hexadecylaminobenzaldehyde Cycloethylene Thioketal

To a mixture of 0.5 g. of p-hexadecylaminobenzaldehyde, 1 g. of anhydrous sodium sulfate, 0.5 g. of freshly fused zinc chloride there is added 10 ml. of ethanedithiol. The reaction mixture is placed in the refrigerator (3°–5° C.) overnight. The excess dimercaptan is evaporated in vacuo, water is added, and the product is extracted with toluene. The extract is washed successively with water, dilute sodium hydroxide and water. It is dried with anhydrous sodium sulfate and an evaporation in vacuo gives a solid residue. Recrystallization from hexanes provides the product of the Example.

EXAMPLE 39 p-Hexadecylaminobenzaldehyde Cycloethylene Hemithioketal

To a mixture of 0.5 g. of p-hexadecylaminobenzaldehyde, 1 g. of anhydrous sodium sulfate, 0.5 g. of freshly fused zinc chloride there is added 10 ml. of β-mercaptoethanol. The mixture is initially cooled to offset an exothermic reaction, and then allowed to stand at room-temperature overnight. Water is added, and the product is extracted with dichloromethane. The latter is washed until neutral, dried and evaporated. Recrystallization from hexanes provides the product of the Example.

EXAMPLE 40 p-Hexadecylaminoacetophenone Cycloethylene Hemithioketal

To a mixture of 0.5 g. of p-hexadecylaminoacetophenone, 1 g. of anhydrous sodium sulfate, and 0.5 g. of freshly fused zinc chloride there is added 10 ml. of β-mercaptoethanol. The mixture is initially cooled to offset an exothermic reaction, and is then allowed to stand at room-temperature overnight. Water is added, and the product is extracted with dichloromethane. The latter is washed with base, then with water until neutral, dried and evaporated. Recrystallization from hexanes provides the product of the Example.

EXAMPLE 41 p-Hexadecylaminobenzaldehyde 1,3-Cyclopropylene Thioketal

To a mixture of 1.0 g. p-hexadecylaminobenzaldehyde, 2 g. of anhydrous magnesium sulfate, and 1.0 g. of freshly fused zinc chloride there is added 1.5 g. of 1,3-propanedithiol. The reaction is allowed to proceed overnight when water is added. The product is extracted with dichloromethane, and the extract is washed with base, water, dried and evaporated. Recrystallization from hexanes provides the product of the Example.

EXAMPLE 42 p-Hexadecylaminobenzaldehyde Ethyl Mercaptal

To a mixture of 1.0 g. of p-hexadecylaminobenzaldehyde, 2 g. of anhydrous magnesium sulfate, and 1.0 g. of freshly fused zinc chloride there is added 1.5 g. of ethyl mercaptan. The reaction is allowed to proceed for 20 hours when water is added. The product is extracted with dichloromethane, and the extract is washed with base, water, dried and evaporated. Chromatography of the residue provides the product of the Example.

EXAMPLE 43 p-Hexadecylaminobenzaldehyde Benzyl Mercaptal

To a mixture of 1.0 g. of p-hexadecylaminobenzaldehyde, 2 g. of anhydrous magnesium sulfate, and 1.0 g. of freshly fused zinc chloride there is added 3 g. of benzyl mercaptan. The reaction is allowed to proceed for 20 hours when water is added. The product is extracted with dichloromethane, and the extract is washed with base, water, dried and evaporated. Chromatography of the residue provides the product of the Example.

EXAMPLE 44 p-Hexadecylaminobenzaldehyde Oxime p-Hexadecylaminobenzaldehyde in ethanol-acetic acid is treated with a concentrated water solution of hydroxylamine hydrochloride. The solid is collected after a brief period, washed with alcohol, and dried to provide the product of the Example.

Use of methoxyamine hydrochloride provides p-hexadecylaminebenzaldehyde methoxime.

EXAMPLE 45 p-Hexadecylaminoacetophenone Methoxime

Following the procedure of Example 44 with p-hexadecylaminoacetophenone provides the product of the Example.

EXAMPLE 46 p-Hexadecylamino-2-oxyacetophenone Hydrazone p-Hexadecylamino-2-oxyacetophenone dissolved in ethanol-acetic acid is treated with aqueous hydrazine solution. The hydrazone precipitates completely after a short time when it is collected by filtration and washed with water.

EXAMPLE 47 p-Hexylaminoacetophenone Phenylhydrazone p-Hexylaminoacetophenone dissolved in ethanol acetic acid is treated with a solution of phenylhydrazine in water-acetic acid. After a short time the phenylhydrazone separates out, and is collected and washed with water.

EXAMPLE 48

| Preparation of 50 mg. Tablets | | |
|---|---|---|
| Per Tablet | | Per 10,000 Tablets |
| 0.050 gm. | Active ingredient | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | | 15 gm. |
| 0.150 gm. | | 1490 gm. |

The active ingredient, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 49

| Preparation of Oral Suspension | |
|---|---|
| Ingredient | Amount |
| Active ingredient | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the active ingredient is suspended therein. The saccharin, sodium benzoate, flavor and dye are added and dissolved. The volume is adjusted to 100 ml. with distilled water. Each ml. of syrup contains 5 mg. of active ingredient.

I claim:

1. A compound selected from the group consisting of those of the formula:

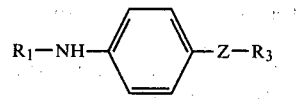

wherein $R_1$ is a straight chain or branched alkyl group of the formula $C_nH_{2n+1}$ wherein n is an integer from 8 to 19, inclusive; $R_3$ is selected from the group consisting of hydrogen, alkyl having up to 6 carbon atoms, lower alkanoy-oxymethyl, phenyl, and phenyl lower alkyl; Z is a divalent radical selected from the group consisting of those of the formulae:

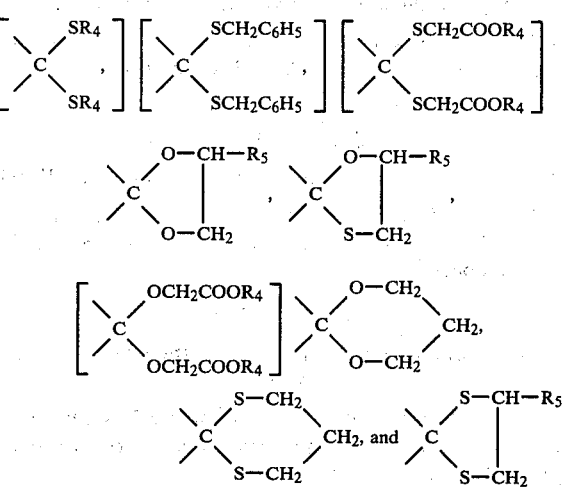

wherein $R_4$ is hydrogen or alkyl having up to 4 carbon atoms and $R_5$ is hydrogen, carboxy, carboxymethyl, hydroxymethyl or alkyl having up to 3 carbon atoms; and the pharmacologically acceptable acid-addition and cationic salts thereof.

2. The compounds of claim 1 in the form of pharmaceutically acceptable acid-addition salts.

3. p-Hexadecylaminobenzaldehyde cycloethylene ketal.

4. p-Hexadecylaminoacetophenone cycloethylene ketal.

5. p-Hexadecylamino-2-oxyacetophenone cycloethylene ketal.

6. p-Hexadecylaminobenzaldehyde cycloethylene hemithioketal.

7. p-Hexadecylaminoacetophenone cycloethylene hemithioketal.

8. p-Hexadecylaminobenzaldehyde 1,3-cyclopropylene thioketal.

* * * * *